United States Patent
Suzuki

(10) Patent No.: US 11,141,667 B2
(45) Date of Patent: Oct. 12, 2021

(54) CONTROL METHOD FOR ATTRACTION APPARATUS AND ATTRACTION SYSTEM

(71) Applicant: Panasonic Intellectual Property Management Co., Ltd., Osaka (JP)

(72) Inventor: Masato Suzuki, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 25 days.

(21) Appl. No.: 16/701,328

(22) Filed: Dec. 3, 2019

(65) Prior Publication Data

US 2020/0101391 A1  Apr. 2, 2020

Related U.S. Application Data

(63) Continuation of application No. PCT/JP2018/019001, filed on May 17, 2018.

(30) Foreign Application Priority Data

Jun. 21, 2017 (JP) .............................. JP2017-121455
Apr. 10, 2018 (JP) .............................. JP2018-075250

(51) Int. Cl.
*A61B 5/1455* (2006.01)
*A63G 31/00* (2006.01)
(Continued)

(52) U.S. Cl.
CPC ............ *A63G 31/00* (2013.01); *A61B 5/0002* (2013.01); *A61B 5/0077* (2013.01); *A61B 5/02* (2013.01);
(Continued)

(58) Field of Classification Search
None
See application file for complete search history.

(56) References Cited

U.S. PATENT DOCUMENTS

| 6,572,511 B1 | 6/2003 | Volpe |
| 2017/0045942 A1 | 2/2017 | Bostick et al. |
| 2017/0332965 A1 | 11/2017 | Hasegawa et al. |

FOREIGN PATENT DOCUMENTS

| JP | 6-142087 | 5/1994 |
| JP | 8-505079 | 6/1996 |

(Continued)

OTHER PUBLICATIONS

International Search Report of PCT application No. PCT/JP2018/019001 dated Aug. 14, 2018.
(Continued)

*Primary Examiner* — Eric F Winakur
*Assistant Examiner* — Marjan Fardanesh
(74) *Attorney, Agent, or Firm* — McDermott Will and Emery LLP

(57) ABSTRACT

An attraction system includes at least one detector, the attraction apparatus, and a controller. The at least one detector detects blood flow information of a user, the attraction apparatus provides at least one stimulus to the user, and the controller is connected to the at least one detector and the attraction apparatus to control the attraction apparatus based on the blood flow information. A control method for the attraction apparatus is executed by the controller and includes: obtaining, from the at least one detector, an amount of change in the blood information before and after the at least one stimulus is provided to the user; and controlling an operation of the attraction apparatus, based on a result of comparison of the amount of change with a threshold.

9 Claims, 9 Drawing Sheets

(51) Int. Cl.
  *A61B 5/026* (2006.01)
  *A61B 5/00* (2006.01)
  *A61B 5/145* (2006.01)
  *A61B 5/02* (2006.01)
  *G06F 3/00* (2006.01)
  *G06F 3/01* (2006.01)

(52) U.S. Cl.
  CPC ........ *A61B 5/0261* (2013.01); *A61B 5/14546* (2013.01); *A61B 5/14553* (2013.01); *A61B 5/742* (2013.01); *A61B 5/7405* (2013.01); *A61B 5/7455* (2013.01); *G06F 3/00* (2013.01); *G06F 3/011* (2013.01)

(56) References Cited

FOREIGN PATENT DOCUMENTS

| | | |
|---|---|---|
| JP | 9-054542 | 2/1997 |
| JP | 10-043429 | 2/1998 |
| JP | 10-127713 | 5/1998 |
| JP | 2004-140812 | 5/2004 |
| JP | 2006-280513 | 10/2006 |
| JP | 2007-202597 | 8/2007 |
| JP | 2007-213539 | 8/2007 |
| JP | 2011-010714 | 1/2011 |
| JP | 2014-053672 | 3/2014 |
| JP | 2014-123883 | 7/2014 |
| JP | 2015-039538 | 3/2015 |
| JP | 2017-532825 | 11/2017 |
| WO | 1995/005223 | 2/1995 |
| WO | 2016/028531 | 2/2016 |
| WO | 2016/084834 | 6/2016 |

OTHER PUBLICATIONS

Roger Marek et al., "The amygdala and medial prefrontal cortex: partners in the fear circuit", J. Physiol. 591.10 (2013), Feb. 18, 2013, pp. 2381-2391.

Philip Tovote et al., "Neuronal circuits for fear and anxiety", Nature Reviews Neuroscience, vol. 16 (2015), Jun. 10, 2015, pp. 317-331.

Hongyu Yang et al., "Gender difference in hemodynamic responses of prefrontal area to emotional stress by near-infrared spectroscopy", Behavioural Brain Research 178 (2007), Jan. 11, 2007, pp. 172-176.

Yusuke Moriguchi et al., "Prefrontal cortex and executive function in young children: a review of NIRS studies", Frontiers in Human Neuroscience, vol. 7, Article 867, Dec. 17, 2013.

Jan Mehnert et al., "Developmental changes in brain activation and functional connectivity during response inhibition in the early childhood brain", Brain & Development 35 (2013), Nov. 12, 2012, pp. 894-904.

Anouk Vermeij et al., "Effects of Aging on Cerebral Oxygenation during Working-Memory Performance: A Functional Near-Infrared Spectroscopy Study", PLOS one, vol. 7, Issue 9, e46210, Sep. 28, 2012.

Evelyn Glotzbach et al., "Prefrontal Brain Activation During Emotional Processing: A Functional Near Infrared Spectroscopy Study (fNIRS)", The Open Neuroimaging Journal, 2011, vol. 5, Jan. 27, 2011, pp. 33-39.

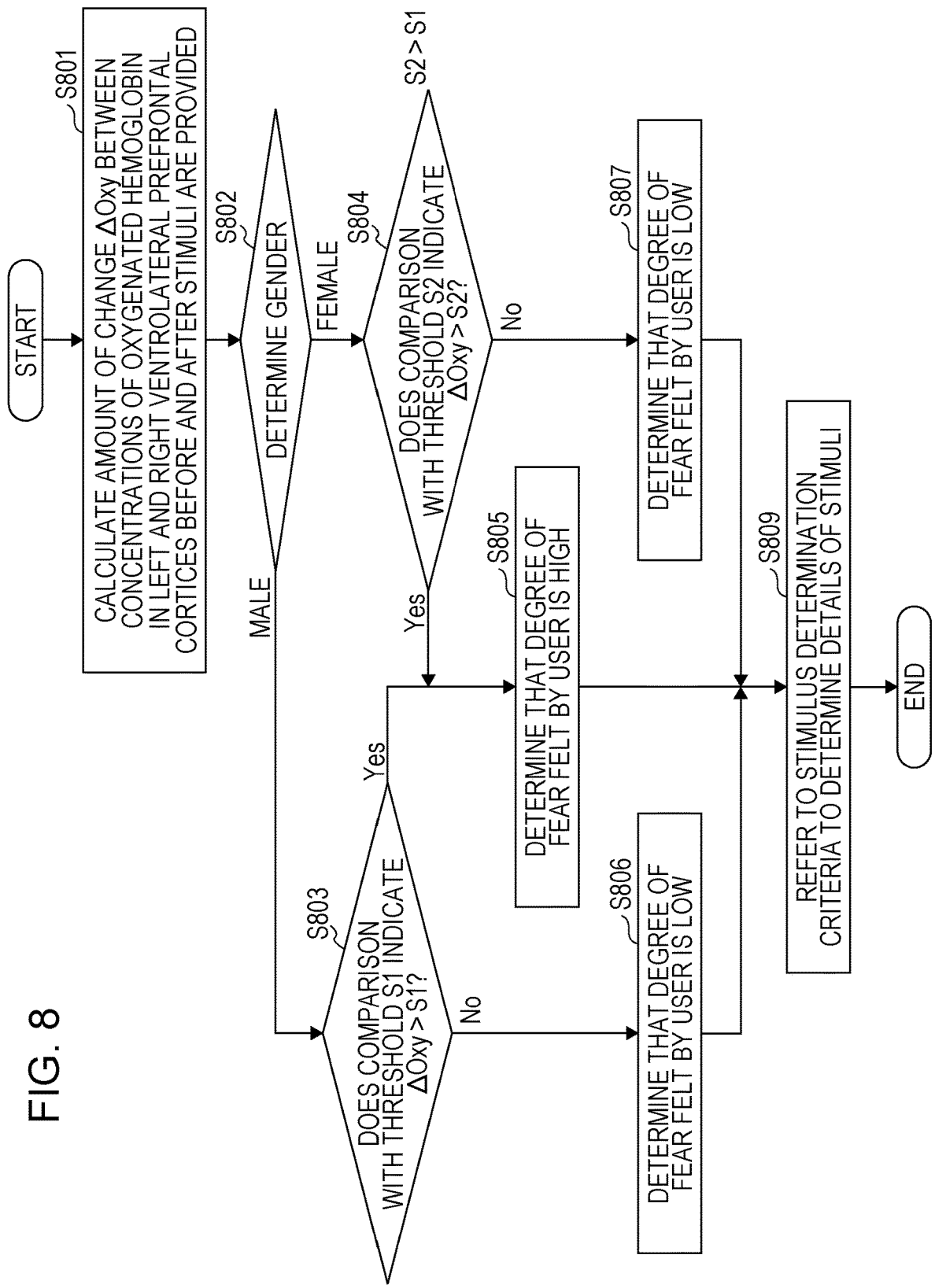

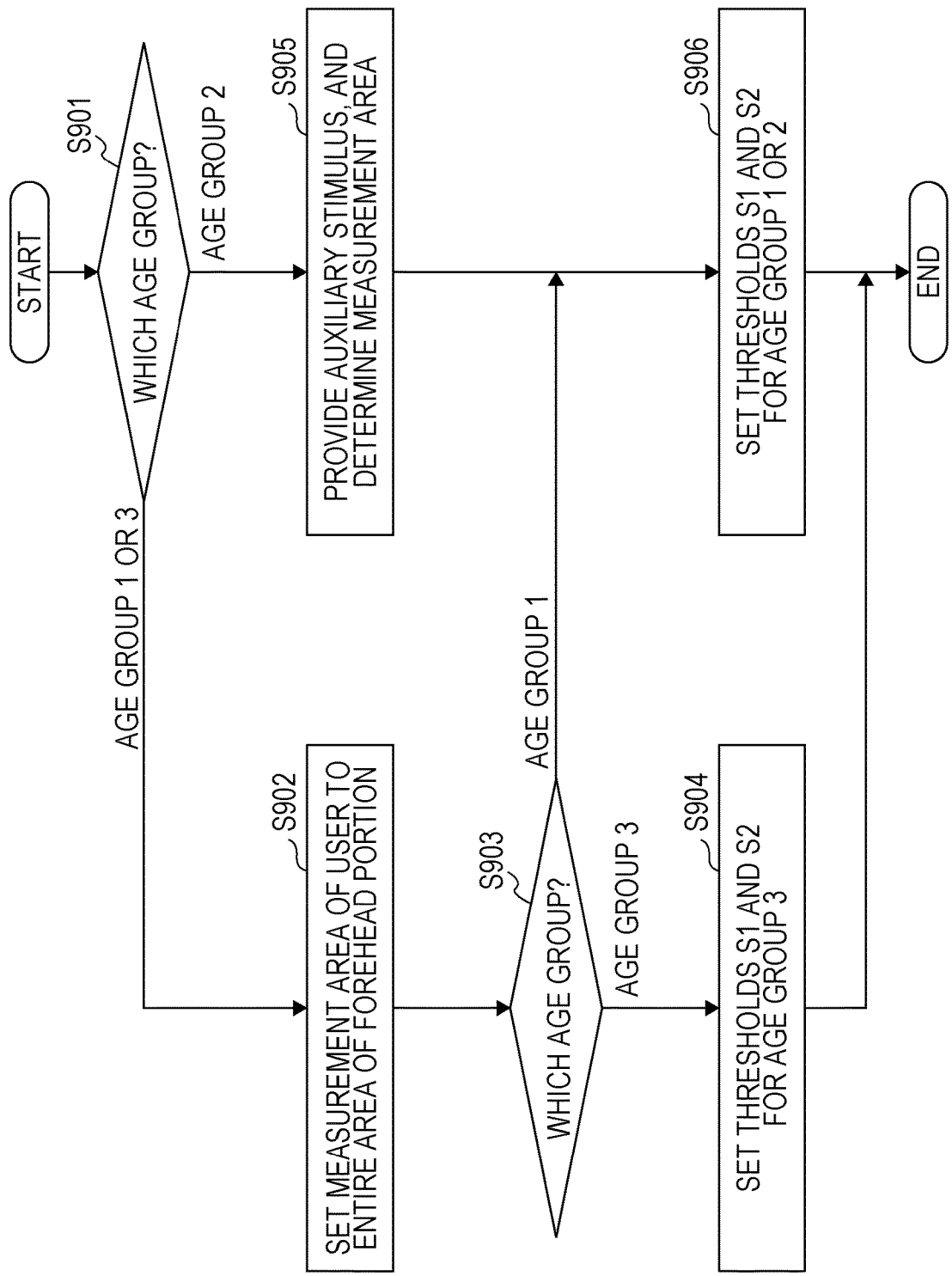

CONTROL METHOD FOR ATTRACTION APPARATUS AND ATTRACTION SYSTEM

BACKGROUND

1. Technical Field

The present disclosure relates to a technology for controlling an attraction apparatus.

2. Description of the Related Art

Various attraction apparatuses are installed at amusement facilities, such as recreation parks, theme parks, and amusement parks. For example, ride attractions, called roller coasters and dark rides, are installed. The roller coasters travel at high speed and make tight turns along a steep railroad track installed high above ground, to thereby give thrills to riders (who may be hereinafter referred to as "users"). The dark rides are mainly installed indoors, and movements of the ride apparatuses are changed in synchronization with video or exhibits to thereby give thrills or surprises to users. A new type of attraction that is a combination of a dark ride and a head-mounted display (HMD) has been introduced in recent years. Dramatically enhancing each user's sense of immersion has been achieved by synchronizing video presented on the HMD and movement of the ride apparatus with each other.

Meanwhile, in systems in which video, such as movies, or games, is provided, a technology for changing video or the degree of difficulty of a game on the basis of living-body information of a user has been known. Examples of such a technology are disclosed in, for example, Japanese Unexamined Patent Application Publication No. 2014-53672 and Japanese Unexamined Patent Application Publication No. 2011-10714.

SUMMARY

In one general aspect, the techniques disclosed here feature a control method for an attraction apparatus in an attraction system including at least one detector, the attraction apparatus, and a controller. The at least one detector detects blood flow information indicating a state of blood flow of a user, the attraction apparatus provides at least one stimulus to the user, and the controller is connected to the at least one detector and the attraction apparatus to control the attraction apparatus based on the blood flow information.

The control method is executed by the controller and includes: obtaining attribute information indicating an attribute of the user; determining a threshold for an amount of change in the blood flow information, based on the attribute information; obtaining first blood flow information of the user from the at least one detector; causing the attraction apparatus to provide a first stimulus to the user; obtaining second blood flow information of the user from the at least one detector, after the first stimulus is provided; obtaining a first amount of change in the blood flow information, based on the first blood flow information and the second blood flow information; and controlling an operation of the attraction apparatus, based on a result of comparison of the first amount of change with the threshold.

It should be noted that general or specific embodiments may be implemented as an apparatus, a device, a system, a method, an integrated circuit, a computer program, or a recording medium. It should also be noted that general or specific embodiments may be implemented as any selective combination of a system, an apparatus, a device, a method, an integrated circuit, a computer program, and a recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is a flowchart specifically illustrating examples of processes in steps S517 and S519 in FIG. 7; and FIG. 9 is a flowchart illustrating an example of processing in a second embodiment.

DETAILED DESCRIPTION

Figure 1:
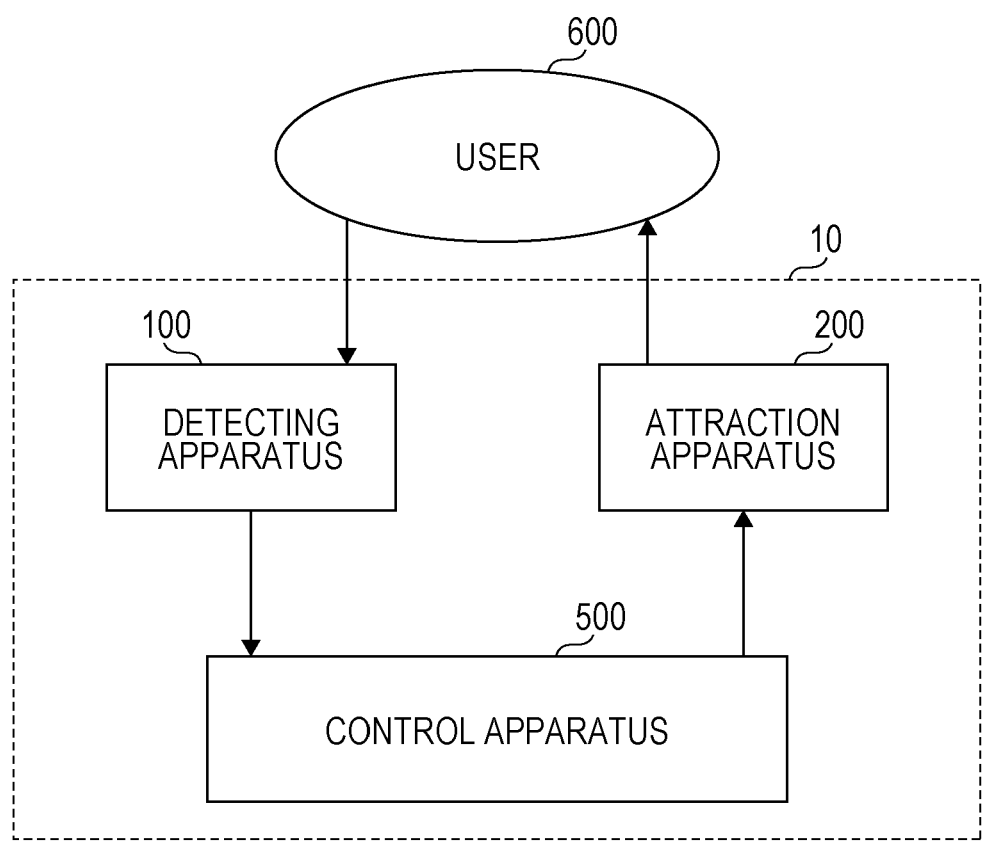
FIG. 1 is a diagram illustrating a schematic configuration of an attraction system in an exemplary embodiment of the present disclosure.

The present disclosure includes a control method, a control apparatus, and an attraction system described in the following items.

[Item 1]

A control method according to a first item of the present disclosure is a control method for an attraction apparatus in an attraction system including at least one detector, the attraction apparatus, and a controller.

The at least one detector detects blood flow information indicating a state of blood flow of a user.

The attraction apparatus provides at least one stimulus to the user.

The controller is connected to the at least one detector and the attraction apparatus to control the attraction apparatus based on the blood flow information.

The control method is executed by the controller and includes:

obtaining attribute information indicating an attribute of the user;

determining a threshold for an amount of change in the blood flow information, based on the attribute information;

obtaining first blood flow information of the user from the at least one detector;

causing the attraction apparatus to provide a first stimulus to the user;

obtaining second blood flow information of the user from the at least one detector, after the first stimulus is provided;

obtaining a first amount of change in the blood flow information, based on the first blood flow information and the second blood flow information; and controlling an operation of the attraction apparatus, based on a result of comparison of the first amount of change with the threshold.

[Item 2]

In the control method according to item 1, the at least one detector may include:

a light source that emits light that illuminates at least one area in the frontal region of the head of the user;

a photodetector that detects reflection light that returns from the at least one area; and a processing circuit that generates the blood flow information of the user, by using information of the reflection light detected by the photodetector.

[Item 3]

The control method according to item 2 may further include:

obtaining third blood flow information of the user, before obtaining the first blood flow information;

causing the attraction apparatus to provide a second stimulus to the user;

obtaining fourth blood flow information of the user from the at least one detector, after the second stimulus is provided;

obtaining a second amount of change in the blood flow information, based on the third blood flow information and the fourth blood flow information; and determining the at least one area to be illuminated with the light during obtaining of the first blood flow information and the second blood flow information, based on the second amount of change.

[Item 4]

In the control method according to item 1, the attribute information may be information indicating the user's gender.

[Item 5]

In the control method according to item 1, the attribute information may be information indicating the user's age.

[Item 6]

In the control method according to item 4 or 5, the attraction system may further include a camera that photographs the user; and the attribute information may be generated based on an image obtained from the camera.

[Item 7]

In the control method according to one of item 1 to 6, the blood flow information may include information indicating a concentration of oxygenated hemoglobin in blood in a brain of the user.

[Item 8]

The control method according to one of items 1 to 7 may further include:

causing the attraction apparatus to provide a third stimulus to the user, after the first amount of change is obtained, wherein the controlling of the operation of the attraction apparatus may include changing an intensity of the third stimulus from an intensity of the first stimulus or changing a type of the third stimulus from a type of the first stimulus, based on a result of comparison of the first amount of change with the threshold.

[Item 9]

In the control method according to item 8, when the first amount of change is smaller than or equal to the threshold, the intensity of the third stimulus may be increased relative to the intensity of the first stimulus.

[Item 10]

In the control method according to one of items 1 to 9, the at least one stimulus may include at least one selected from a group consisting of video, sound, movement, tactile sensation, and smell.

[Item 11]

In the control method according to one of items 1 to 10, the attraction apparatus may be a ride apparatus that the user is able to ride.

[Item 12]

In the control method according to one of items 1 to 11, the at least one stimulus may include video, and the attraction system may further include a display that provides the video to the user.

[Item 13]

In the control method according to item 12, the attraction system may further include a head-mounted display including the at least one detector and the display, and the control method may further include:

synchronously controlling the operation of the attraction apparatus and display of the video on the display; and changing the video, based on the result of the comparison of the first amount of change with the threshold.

[Item 14]

In the control method according to one of items 1 to 13, the at least one detector may include a plurality of detectors;

the plurality of detectors may detect blood flow information of users, respectively;

the attraction apparatus may individually provide the at least one stimulus to each of the users;

the controller may be connected to the plurality of detectors and the attraction apparatus;

the determining of the threshold may include determining the threshold for each of the users, based on the attribute information;

the obtaining of the first blood flow information may include obtaining the first blood flow information of each of the users from a corresponding one of the plurality of detectors;

the providing of the first stimulus may include causing the attraction apparatus to provide the first stimulus to each of the users;

the obtaining of the second blood flow information may include obtaining the second blood flow information of each of the users from the corresponding one of the plurality of detectors, after the first stimulus is provided;

the obtaining of the first amount of change may include obtaining the first amount of change for each of the users, based on the first blood flow information and the second blood flow information; and the controlling of the operation of the attraction apparatus may include individually controlling the operation of the attraction apparatus for each of the users, based on the result of the comparison of the first amount of change with the threshold.

[Item 15]

An attraction system according to another aspect of the present disclosure includes:

at least one detector that detects blood flow information indicating a state of blood flow of a user;

an attraction apparatus that provides at least one stimulus to the user; and a control apparatus that is connected to the at least one detector and the attraction apparatus to control the attraction apparatus based on the blood flow information.

The at least one detector includes:

a light source that emits light that illuminates at least one area in the frontal region of the head of the user;

a photodetector that detects reflection light that returns from the at least one area; and a processing circuit that generates the blood flow information of the user, by using information of the reflection light detected by the photodetector.

The controller includes:

a control circuit; and a recording medium in which a computer program is stored.

The computer program causes the control circuit to execute:

obtaining attribute information indicating an attribute of the user;

determining a threshold for an amount of change in the blood flow information, based on the attribute information;

obtaining first blood flow information of the user from the at least one detector;

causing the attraction apparatus to provide a first stimulus to the user;

obtaining second blood flow information of the user from the at least one detector, after the first stimulus is provided;

obtaining a first amount of change in the blood flow information, based on the first blood flow information and the second blood flow information; and controlling an operation of the attraction apparatus, based on a result of comparison of the first amount of change with the threshold.

[Item 16]

In the attraction system according to item 15, the at least one detector may include a plurality of detectors;

the plurality of detectors may detect blood flow information of users, respectively;

the attraction apparatus may individually provide the at least one stimulus to each of the users; and the controller may be connected to the plurality of detectors and the attraction apparatus.

The determining of the threshold may include determining the threshold for each of the users, based on the attribute information;

the obtaining of the first blood flow information may include obtaining the first blood flow information of each of the users from a corresponding one of the plurality of detectors;

the providing of the first stimulus may include causing the attraction apparatus to provide the first stimulus to each of the users;

the obtaining of the second blood flow information may include obtaining the second blood flow information of each of the users from the corresponding one of the plurality of detectors, after the first stimulus is provided;

the obtaining of the first amount of change may include obtaining the first amount of change for each of the users, based on the first blood flow information and the second blood flow information; and the controlling of the operation of the attraction apparatus may include individually controlling the operation of the attraction apparatus for each of the users, based on the result of the comparison of the first amount of change with the threshold.

[Item 17]

A control method according to another aspect of the present disclosure is a control method for a blood-flow-information detection system that includes:

a stimulation device that provides a stimulus to a user;

a light source that emits light that illuminates at least one area in the frontal region of the head of the user;

a photodetector that detects reflection light that returns from the at least one area; and a processing circuit that generates blood flow information indicating a state of blood flow of the user, by using information of the reflection light detected by the photodetector.

The control method includes:

causing the light source to emit the light;

causing the stimulation device to provide the stimulus to the user;

causing the blood-flow-information detection system to detect first blood flow information of the user under a detection condition, when the stimulus is provided and/or after the stimulus is provided; and updating the detection condition, based on the first blood flow information.

[Item 18]

In the control method according to item 17, in the updating of the detection condition, the light emission by the light source may be controlled.

[Item 19]

In the control method according to item 17, in the updating of the detection condition, the at least one area to be illuminated with the light may be changed.

[Item 20]

The control method according to item 17 may further include:

causing the blood-flow-information detection system to detect second blood flow information of the user, before the stimulation device is caused to provide the stimulus to the user; and the updating of the detection condition may be performed based on a result of comparison between the first blood flow information and the second blood flow information.

[Item 21]

In the control method according to item 17, the blood-flow-information detection system may be an attraction system.

[Item 22]

A non-transitory computer-readable recording medium according to another aspect of the present disclosure is a computer-readable recording medium storing therein a program for controlling a blood-flow-information detection system including:

a stimulation device that provides a stimulus to a user;

a light source that emits light that illuminates at least one area in the frontal region of the head of the user;

a photodetector that detects reflection light that returns from the at least one area; and a processing circuit that generates blood flow information indicating a state of blood flow of the user, by using information of the reflection light detected by the photodetector.

The program, when executed by a computer, causes the computer to execute:

causing the light source to emit the light;

causing the stimulation device to provide the stimulus to the user;

causing the blood-flow-information detection system to detect first blood flow information of the user under a detection condition, when the stimulus is provided and/or after the stimulus is provided; and updating the detection condition, based on the first blood flow information.

[Item 23]

A blood-flow-information detection system according to yet another aspect of the present disclosure includes:

a stimulation device that provides a stimulus to a user;

a light source that emits light that illuminates at least one area in the frontal region of the head of the user;

a photodetector that detects reflection light that returns from the at least one area; and a processing circuit that generates blood flow information indicating a state of blood flow of the user, by using information of the reflection light detected by the photodetector, and when the stimulus is provided and/or after the stimulus is provided, first blood flow information of the user is detected under a detection condition; and the detection condition is updated based on the blood flow information.

In the present disclosure, all or a part of any of circuits, units, apparatuses, devices, parts, or portions or any of functional blocks in the block diagrams may be implemented as one or more of electronic circuits including, but not limited to, a semiconductor device, a semiconductor integrated circuit (IC), or a large-scale integration (LSI). The LSI or IC can be integrated into one chip or also can be a combination of a plurality of chips. For example, functional blocks other than a memory may be integrated into one chip. Although the name used here is an LSI or IC, it may also be called a system LSI, a very large scale integration (VLSI), or an ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can also be used for the same purpose.

In addition, the functions or operations of all or a part of the circuits, units, apparatuses, devices, parts, or portions can be implemented by executing software. In such a case, the software is recorded on one or more non-transitory recording media, such as a ROM, an optical disk, or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

The present disclosure relates to, for example, an attraction system in which amusement facilities are installed, a control apparatus that is used in the attraction system, and a control method and a computer program that are executed by the control apparatus. The attraction system includes a detecting apparatus that detects living-body information of a user, an attraction apparatus, and a control apparatus. The control apparatus controls the operation of the attraction apparatus, based on living-body information that varies depending on the psychological state of the user. Thus, an appropriate stimulus corresponding to the psychological state of the user is provided to the user, thus making it possible to further enhance the degree of satisfaction.

The "attraction apparatus" as used herein refers to, for example, an apparatus that is installed at an amusement facility, such as a recreation park, a theme park, or an amusement park, to provide at least one stimulus to a user. Examples of the stimulus provided by the attraction apparatus include stimuli involving video, sound, movement, tactile sensation, smell, heat, and cold sensation. The attraction apparatus gives at least one of the stimuli to a user to thereby stimulate at least one of five senses of the user. Examples of the attraction apparatus include ride apparatuses used in ride attractions, such as a roller coaster and a dark ride. The attraction apparatus may be an apparatus that is used in attractions other than ride attractions.

The control apparatus controls the attraction apparatus. The control apparatus has, for example, a control circuit, which is a computational processing circuit, such as a central processing unit (CPU), and a recording medium, such as a memory. The control circuit in the control apparatus controls the operation of the attraction apparatus by executing a computer program (hereinafter referred to simply as a "program") recorded in a recording medium.

First Embodiment

FIG. 1 is a diagram illustrating a schematic configuration of an attraction system 10 in an exemplary first embodiment of the present disclosure. The attraction system 10 includes a detecting apparatus 100, an attraction apparatus 200, and a control apparatus 500. The control apparatus 500 is connected to the detecting apparatus 100 and the attraction apparatus 200 to control them.

The attraction apparatus 200 in the present embodiment is an apparatus that is installed at an amusement facility to provide at least one stimulus to at least one user 600. The attraction apparatus 200 is not a home video game console. That is, the attraction apparatus 200 is not an apparatus that is used in a general household and in which a game proceeds as a user operates a controller or the like, for example, like a game console disclosed in Japanese Unexamined Patent Application Publication No. 2011-10714. However, a control method, which is described below in detail, can also be applied to appliances, such as home video game consoles, that are used for entertainment purposes and are used at places other than amusement facilities.

The detecting apparatus 100 detects living-body information that changes according to a psychological state of each user 600. The living-body information may be, for example, blood flow information indicating the state of blood flow in a target portion of each user 600. The target portion is, for example, the frontal region of the head and may be another portion. The blood flow information that can be detected by the detecting apparatus 100 is, for example, information of cerebral blood flow or information of skin blood flow. The cerebral blood flow information or the skin blood flow information of the frontal region can be obtained, for example, by illuminating at least one area in the forehead portion of the user 600 with light, such as near-infrared light, and detecting reflection light therefrom. The living-body information is not limited to the blood flow information and may be any information in which the psychological state of the user 600 is reflected. For example, a temperature or an electrical resistance of skin of the user 600, the heart rate thereof, or the like may also be used as the living-body information.

The control apparatus 500 obtains living-body information from the detecting apparatus 100 and controls the operation of the attraction apparatus 200 based on the obtained living-body information. By using the obtained living-body information, the control apparatus 500 can estimate the psychological state of the user 600. For example, when the living-body information includes information regarding the concentration of oxygenated hemoglobin in blood in the brain of the user 600, the control apparatus 500 can estimate whether or not the user 600 is feeling fear, based on the concentration of the oxygenated hemoglobin. Upon determining that the user 600 is not feeling much fear, based on the living-body information, such as the cerebral blood flow information, the control apparatus 500 strengthens the stimulus given to the user 600, to make it possible to make the user 600 feel more fear.

In order to realize such control, for example, the control apparatus 500 may obtain pieces of blood flow information of the user 600 before and after the attraction apparatus 200 gives the stimulus to the user 600 and may estimate the psychological state of the user 600 based on comparison between the pieces of blood flow information. For example, when a change between the oxygenated hemoglobin concentrations obtained from the pieces of cerebral blood flow information of the user 600 before and after the stimulation is larger than a threshold, the control apparatus 500 can estimate that the user 600 is feeling fear due to the stimulus.

Changes in the living-body information with respect to a stimulus differ from one person to another and also tend to differ depending on the genders. For example, according to Yang H. et al., "Gender difference in hemodynamic responses of prefrontal area to emotional stress by near-infrared spectroscopy" Behavioural Brain Res., 178 (2007) 172-176 (hereinafter referred to as "Non-Patent Document 1"), it is found that women have larger amounts of change in the oxygenated hemoglobin in response to stimuli than men. Thus, adjustment, such as varying a threshold used for determining the psychological state of the user 600, may be performed depending on his or her gender.

Changes in the living-body information in response to stimuli also tend to differ depending on age groups. For example, it is known that, in three segments "infants", "adults", and "elderly people", the cerebral blood flow in the prefrontal area varies in different areas and with different intensities. Accordingly, adjustment, such as varying a threshold used for determining the psychological state of the user 600 or changing a detection portion, may be performed depending on the age group of the user 600.

Thus, based on attribute information indicating an attribute of the user 600, such as the gender or the age group, the control apparatus 500 in the present embodiment varies a threshold for the amount of change in the blood flow information of the user 600 and/or changes the detection portion. The control circuit executes operations below:

(1) causing the detecting apparatus to obtain first blood flow information of a user;
(2) causing the attraction apparatus to provide a first stimulus to the user;
(3) causing the detecting apparatus to obtain second blood flow information of the user after the first stimulus is provided;
(4) calculating a first amount of change in the blood flow information, based on the first blood flow information and the second blood flow information; and
(5) controlling the operation of the attraction apparatus, based on a result of comparison of the first amount of change with a threshold.

According to such an attraction-apparatus control method, a stimulus provided to each user can be appropriately controlled based on emotion, such as fear, felt by each user during operation of the attraction apparatus. For example, the intensity of the stimulus, such as content of video, an audio volume, acceleration of the ride apparatus, the amount of wind, or smell, provided to each user can be controlled for the user. This makes it possible to enhance the sense of satisfaction of each user.

In FIG. 1, each of the detecting apparatus 100, the attraction apparatus 200, and the control apparatus 500 is represented as one block. However, the detecting apparatus 100, the attraction apparatus 200, and the control apparatus 500 do not necessarily have to be configured as independent apparatuses in appearance. For example, the control apparatus 500 may be incorporated into the attraction apparatus 200 or the detecting apparatus 100. Alternatively, all the detecting apparatus 100, the attraction apparatus 200, and the control apparatus 500 may be included in a single integrated apparatus. The control apparatus 500 may be connected with the detecting apparatus 100 and the attraction apparatus 200 through cable or wireless connections. The control apparatus 500 may also be connected with the detecting apparatus 100 and the attraction apparatus 200, for example, through the Internet or a remote network. In other words, the control apparatus 500 may be realized by a server computer provided in a cloud.

(Principle)

Next, a principle for the detecting apparatus 100 to measure living-body information will be described with reference to FIG. 2.

Figure 2:
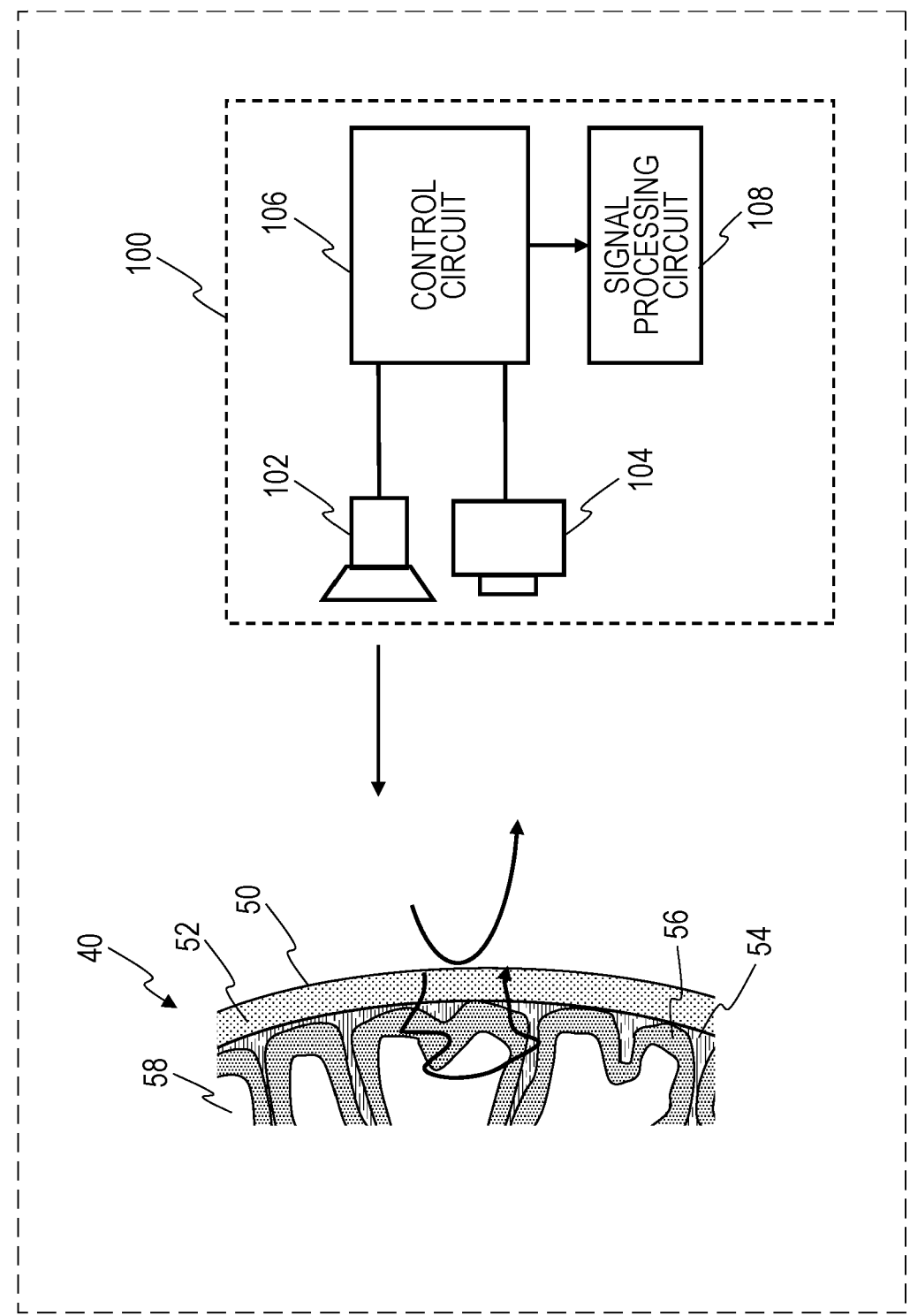
FIG. 2 is a diagram schematically illustrating a configuration example of a detecting apparatus.

FIG. 2 is a diagram schematically illustrating a configuration example of the detecting apparatus 100. FIG. 2 also illustrates a target portion 40 of a user. The target portion 40 in this example is the forehead portion of the user.

The detecting apparatus 100 includes a light source 102, a photodetector 104, a control circuit 106, and a signal processing circuit 108. The light source 102 emits light to the target portion 40 of the user. The photodetector 104 detects light emitted from the light source 102 and reflected by the target portion 40. The control circuit 106 is connected to the light source 102 and the photodetector 104 to control operations thereof. The signal processing circuit 108 generates cerebral blood flow information of the user, based on signals of the light detected by the photodetector 104, and outputs the cerebral blood flow information.

The detecting apparatus 100 in this example obtains the blood flow information of the user by performing living-body measurement using near-infrared spectroscopy (NIRS). In this living-body measurement method, the light source 102 illuminates the forehead portion of a human body with near-infrared light. Part of the light with which the forehead portion is illustrated is diffusely reflected in tissue in the brain, such as grey matter 56, which is the cerebral cortex, exits the head portion, and returns toward the detecting apparatus 100. Upon receiving the light that has returned, the photodetector 104 outputs electrical signals corresponding to the amount of the received light. Based on the electrical signals, the signal processing circuit 108 detects changes in the amount of the received light to generate blood flow information indicating the state of blood flow in the brain or scalp.

The light emitted from the light source 102 is not limited to near-infrared light and may be visible light having a wavelength that is close to that of the near-infrared light. The wavelength of the light that is used may be any wavelength over which information of at least one of cerebral blood flow and skin blood flow is obtained, and is, for example, a wavelength of about 600 to 1400 nm.

As illustrated in FIG. 2, a skull 52 lies inside a scalp 50 of the human body. A cerebrospinal fluid 54, the grey matter 56, and white matter 58 lie inside the skull 52. Part of the light emitted from the light source 102 to the target portion 40 is reflected by the scalp 50 and travels to the photodetector 104. Other part of the light emitted from the light source 102 passes through the skull 52 and reaches the grey matter 56 and the white matter 58. Part of the light that has entered the head portion is absorbed by hemoglobin in blood in the brain or the scalp 50. Part of light that has not absorbed is repeatedly reflected by brain tissue, such as the grey matter 56 and the white matter 58. Part of the reflected light exits the scalp 50 and travels to the photodetector 104. By using an electronic shutter function provided by the control circuit 106, the photodetector 104 detects at least part of the light reflected by the scalp 50 and the light that passes through the brain tissue and returns. The arrows in FIG. 2 represent one example of light propagation paths in the process described above.

When people think or do physical exercise, the amount of blood increases in active areas in the brain. As the amount of blood increases, the concentration of hemoglobin increases. When the concentration of hemoglobin increases, the absorption rate of light increases, thus reducing the amount of light detected by the photodetector 104. Meanwhile, it is also known that, owing to functions of autonomic nerves, the skin blood flow also changes, reflecting the psychological state. Accordingly, detecting changes in the amount of light detected by the photodetector 104 makes it possible to recognize the state of blood flow in the brain or the scalp.

In the example illustrated in FIG. 2, the light emitted from the light source 102 is light having a single wavelength. The light is not limited to this example and may be a combination of light having a plurality of wavelengths. For example, the light may be a combination of light having a wavelength that is larger than or equal to 650 nm and that is smaller than a wavelength of 805 nm and light having a wavelength that is larger than 805 nm and that is smaller than or equal to 950 nm. Such a configuration in which light having a plurality of wavelengths is combined is particularly effective in performing control based on the ratio of the concentration of oxygenated hemoglobin to the concentration of deoxygenated hemoglobin. The absorption rate of the oxygenated hemoglobin and the absorption rate of the deoxygenated hemoglobin differ in the aforementioned two wavelength ranges. Thus, computing two electrical signals obtained using two types of light belonging to the two wavelength ranges makes it possible to measure the rates of oxygenated hemoglobin and deoxygenated hemoglobin in blood in the brain.

The control circuit 106 synchronously controls the timing of the light illumination by the light source 102 and the timing of the detection by the photodetector 104. The signal processing circuit 108 processes electrical signals indicating the amount of light detected by the photodetector 104. Based on the electrical signals, the signal processing circuit 108 generates, for example, a signal indicating a concentration distribution of oxygenated hemoglobin and outputs the signal as blood flow information. This blood flow information is transmitted to the control apparatus 500 illustrated in FIG. 1.

Based on the blood flow information obtained from the detecting apparatus 100, the control apparatus 500 controls the operation of the attraction apparatus 200. For example, in accordance with changes in the blood flow information, the control apparatus 500 varies the intensity or the type of at least one stimulus provided from the attraction apparatus 200 to the user. This makes it possible to make, for example, a user who is not feeling fear during an attraction feel fear, by giving a stimulus having a larger intensity or a different type of stimulus to the user.

The attraction system 10 may include a plurality of detecting apparatuses 100, and the detecting apparatuses 100 may be configured to be able to detect pieces of blood flow information of corresponding users 600. The attraction apparatus 200 may be configured to be able to individually control stimuli to be given to the respective users 600. In such a configuration, the control apparatus 500 obtains the pieces of blood flow information of the respective users 600 from the corresponding detecting apparatuses 100 and individually control the stimuli to be given to the users 600 based on the pieces of blood flow information of the respective users 600.

For example, as described in Marek R. et al., "The amygdala and medial prefrontal cortex: partners in the fear circuit" J. Phsiol. 591.10 (2013) 2381-2391 (Non-Patent Document 2) and Tovote P. et al., "Neuronal circuits for fear and anxiety" Nat. Rev Neurosci., 16 (2015) 317-331 (Non-Patent Document 3), an emotion of fear is known to be deeply associated with the amygdala and the prefrontal area in the brain. When a stimulus for evoking an emotion of fear is provided to a target person, this information is transmitted from the thalamus to the sensory area and reaches the prefrontal area. The information is further transmitted from the prefrontal area to the amygdala, and as a result, an emotion of fear is thought to arise in the amygdala. Accordingly, if the brain activity in the prefrontal area can be measured using an optical method, it is possible to assume whether or not the target person has an emotion of fear.

Figure 3:
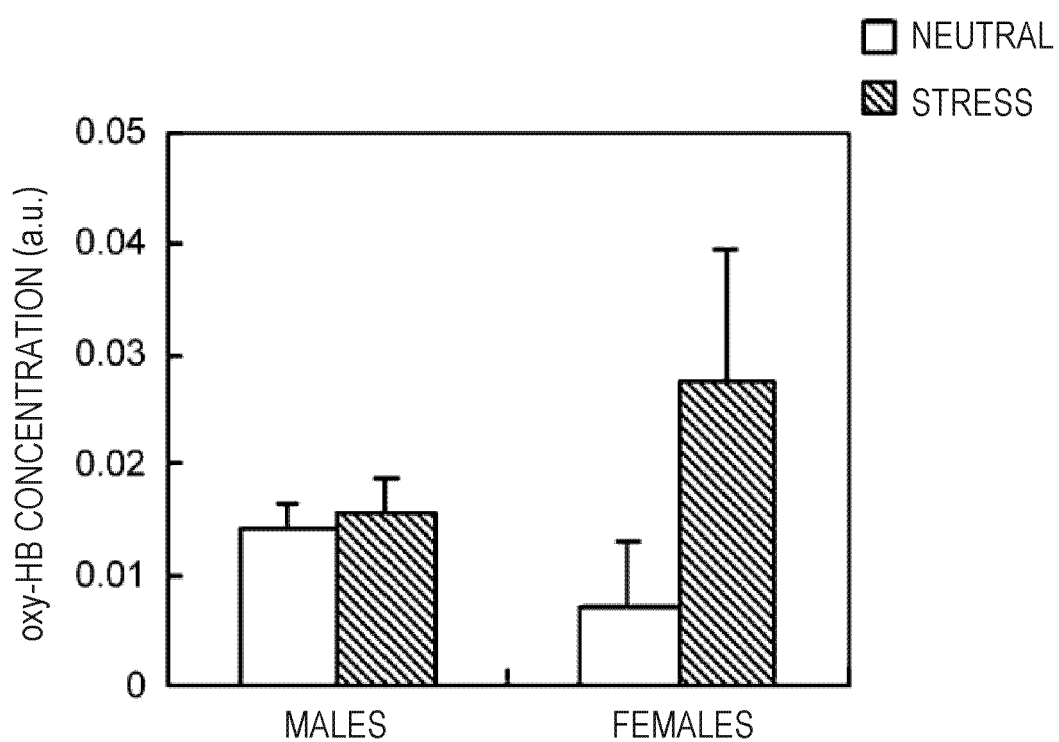
FIG. 3 is a graph illustrating a result of an experiment disclosed in a prior document.

Meanwhile, Non-Patent Document 1 discloses an experiment in which the amounts of oxygenated hemoglobin in the prefrontal areas of a plurality of target people are measured when video for evoking an emotion of fear is presented thereto. According to the result of the experiment, when the video for evoking an emotion of fear is presented, the amounts of oxygenated hemoglobin increase, compared with a case in which normal video is presented. The result further shows that there is a difference in the amounts of change between men and women. FIG. 3 in Non-Patent Document 1 is incorporated as FIG. 3 herein for reference. FIG. 3 illustrates a result of the experiment disclosed in Non-Patent Document 1. Table 1 below illustrates the result of the experiment. Numerical values shown in Table 1 indicate concentrations of oxygenated hemoglobin measured when a neutral stimulus or a fearful stimulus, which is a stimulus for evoking an emotion of fear, was given.

TABLE 1

|  | Neutral Stimulus | Fearful Stimulus | Rate of Increase |
| --- | --- | --- | --- |
| Males | 0.0141 | 0.0156 | 1.11 times |
| Females | 0.0071 | 0.0279 | 3.93 times |

In this experiment, the average value of the concentrations of oxygenated hemoglobin when normal video, which is a neutral stimulus, was presented to males was 0.0141, and the average value of the concentrations of oxygenated hemoglobin when video for evoking an emotion of fear, the video being a fearful stimulus, was presented to the males was 0.0156. On the other hand, the average value of the concentrations of oxygenated hemoglobin when normal video was presented to females was 0.0071, and the average value of the concentrations of oxygenated hemoglobin when video for evoking an emotion of fear was presented to the females was 0.0279.

According to this experiment, the rate of increase in the concentrations of oxygenated hemoglobin when the video for evoking an emotion of fear was presented was only 1.11 times for the males and was 3.93 times, which was a large value, for the females. This result shows a large gender difference in the rate of change in oxygenated hemoglobin in response to fear. Although this experiment was conducted on the concentrations of oxygenated hemoglobin, there is also a gender difference in other living-body information, such as heart rates.

Accordingly, when an attraction apparatus is controlled based on the living-body information, performing control considering the gender of each user is thought to be effective. For example, a technique in which the information regarding the cerebral blood flow or the scalp blood flow obtained by the above-described detecting apparatus is combined with the gender information and an appropriate threshold for the amount of change in the concentration of oxygenated hemoglobin is set is thought to be effective. A determination as to whether or not the user is feeling fear can be more accurately made based on whether or not the rate of increase in the concentration of oxygenated hemoglobin after presentation of a stimulus relative to the concentration of oxygenated hemoglobin during a normal state exceeds a threshold determined based on the gender.

It is thought that the prefrontal area of the brain is associated with display of high-level cerebral functions and particularly performs executive functions. The executive functions are considered to be constituted by three elements. The three elements are inhibition, task rule shifting, and information updating. As described in Yusuke Moriguchi and Kazuo Hiraki (2013) "Prefrontal cortex and executive function in young children: a review of NIRS studies" Frontiers in Human Neurosci., 17, Article 967 (hereinafter referred to as "Non-Patent Document 4"), the executive functions are essential for people to adapt to complex tasks in the social environment and are considered to develop substantially from infancy through adolescence. For example, Mehnert J., Akhrif A., Telkemeyer S., Rossi S., Schmitz C. H., Steinbrink J., et al. (2013). "Developmental changes in brain activation and functional connectivity during response inhibition in the early childhood brain." Brain Dev. 35, 894-904. doi:10.1016/j.braindev.2012.11.006 (Non-Patent Document 5) reports that cerebral blood flow response in the prefrontal area while executing a go/no-go task differs between 6-year old children and adults. The go/no-go task is a task in which target people are instructed to press a button when a target is presented (go condition) and not to press the button when a non-target is presented (no-go condition). According to Non-Patent Document 5, the adults activate the right frontal cortices during no-go execution, and the 6-year old children activate the right frontal cortices in both go and no-go execution. This is possibly because since the executive functions of adults have developed fully, the executive functions work when the no-go target, which requires inhibition, is presented, and the cerebral blood flow in the right frontal cortices increase. On the other hand, since control on the executive functions of 6-year-old children is immature, the cerebral blood flow is thought to increase when either of the tasks is presented.

In addition, the executive functions are known to decline with aging. For example, changes in the cerebral blood flow in the prefrontal areas of healthy young adults aged from 21 to 32 and healthy older adults aged from 64 to 81 during execution of N-back tasks, which are known as tasks for examining the executive functions, were measured in Anouk Vermeij, Arenda H. E. A. van Beek, Marcel G. M. Olde Rikkert, Jurgen A. H. R. Claassen, Roy P. C. Kessels(2012) "Effects of Aging on Cerebral Oxygenation during Working-Memory Performance: A Functional Near-Infrared Spectroscopy Study" PLOS one, 7, e46210 (Non-Patent Document 6). In the measurement, the group of young adults showed increases in the cerebral blood flow during execution of the tasks, particularly, significant increases in the cerebral blood flow in the right brains, whereas the older adults showed equal increases in the cerebral blood flow in the left and right brains.

Thus, in three segments "infants", "adults", and "elderly people", the cerebral blood flow in the prefrontal area varies in different areas and with different intensities during activation of an executive function. Evelyn Glotzbach, Andreas Muhlberger, Kathrin Gschwendtner, Andreas J Fallgatter, Paul Pauli, and Martin J Herrmann (2011) "Prefrontal Brain Activation During Emotional Processing: A Functional Near Infrared Spectroscopy Study (fNIRS)" Open Neuroimaging. J., 5, 33-39 (Non-Patent Document 7) reports that the cerebral blood flow in the prefrontal area not only changes during activation of the executive functions but also changes during emotional processing. When fearful pictures were presented to healthy women to cause the women to express emotions of fear, the cerebral blood flow in the left and right prefrontal areas increased, and when an instruction for suppressing the emotions of fear was given, the cerebral blood flow in the prefrontal areas in the left brains increased prominently.

In view of the foregoing, when an attraction apparatus gives an emotional stimulus to a rider thereof, it is thought that changes in the cerebral blood flow in the prefrontal area of the rider are induced. The amount of change induced in the cerebral blood flow and an area in which the cerebral blood flow changes are assumed to depend on the rider's gender and generation and a display form of emotion of the rider. The display form of emotion is that the rider straightforwardly expresses his or her emotion or tries to suppress his or her emotion without expressing the emotion when he or she feels it.

Accordingly, all or part of attribute information, such as the gender or the age group of the rider, and blood flow information when a preliminary stimulus is given may be obtained before the start of the actual attraction or in the middle of the attraction, and this method is thought to be effective. The emotional state of the rider can be estimated based on the obtained information. For example, a threshold for the amount of change in the cerebral blood flow information which is used in order to estimate the emotional state of the rider and/or a detection portion that is an area from which the cerebral blood flow information is obtained can be determined or varied based on the obtained information.

The following description will be given of a more specific embodiment based on of fear state analogy as described above. However, an overly detailed description may be omitted herein. For example, a detailed description of already well-known things and a redundant description of substantially the same configuration may be omitted herein. This is to avoid the following description becoming overly redundant and to facilitate understanding of those skilled in the art. The accompanying drawings and the following description are provided so as to allow those skilled in the art to fully understand the present disclosure and are not intended to limit the subject matters recited in the claims. In the following description, the same or similar constituent elements are denoted by the same reference numerals.

(Configurations)

Figure 4:
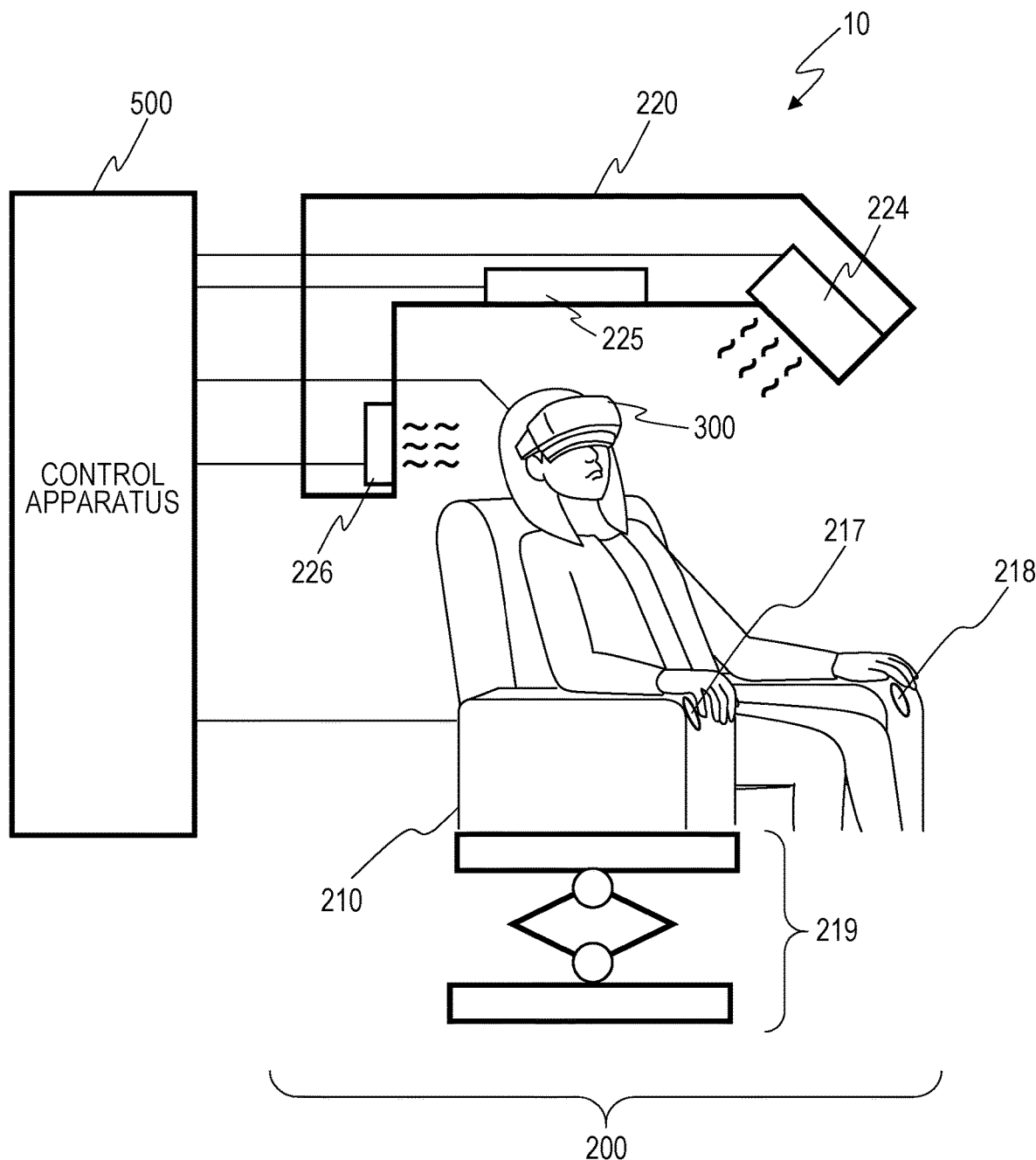
FIG. 4 is a view schematically illustrating the configuration of the attraction system.

FIG. 4 is a view schematically illustrating the configuration of the attraction system 10 in the exemplary embodiment of the present disclosure. FIG. 4 also illustrates a user who uses the attraction system 10. This attraction system 10 includes a head-mounted display 300 having a detecting apparatus and a display that are built therein, the attraction apparatus 200 that provides various stimuli to the user, and the control apparatus 500. The attraction apparatus 200 includes a ride apparatus 210 and a stimulation unit 220. The ride apparatus 210 include a physiological-information measurement device 217, a skin stimulation device 218, and a movement stimulation device 219. The stimulation unit 220 includes a blowing device 224, an acoustic device 225, and a smell generating device 226.

In the present embodiment, although the stimulation unit 220 is separated from the head-mounted display 300 and the ride apparatus 210, the stimulation unit 220 may be built into the head-mounted display 300 and the ride apparatus 210. The head-mounted display 300, the ride apparatus 210, and the stimulation unit 220 are connected to the control apparatus 500. A method for the connection may be a method using cable or wireless connections.

Figure 5:
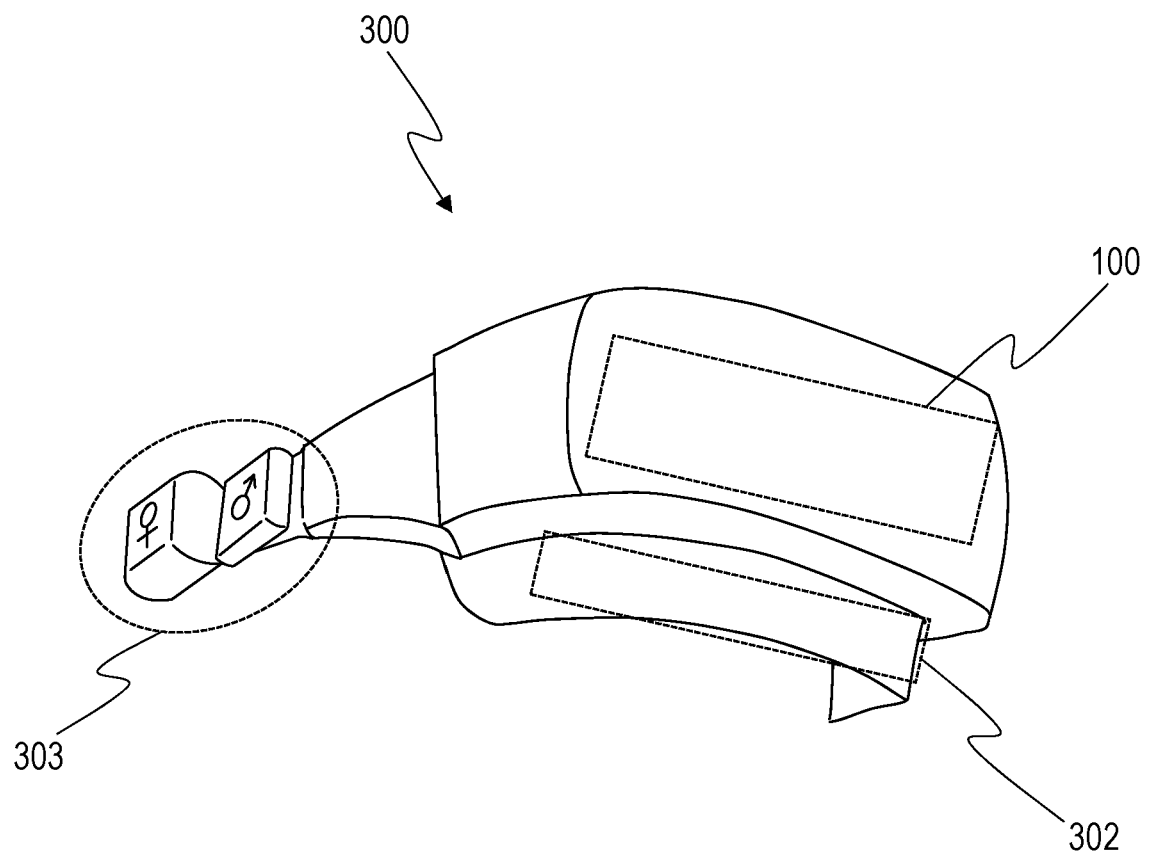
FIG. 5 is a view illustrating a configuration example of a head-mounted display.

FIG. 5 is a view illustrating a configuration example of the head-mounted display 300. The head-mounted display 300 includes the detecting apparatus 100, a display 302, and a gender input device 303. The detecting apparatus 100 has the configuration illustrated in FIG. 2 and obtains cerebral blood flow information of a user of the attraction apparatus 200 in accordance with the principle described above. The display 302 is, for example, a liquid crystal display or an organic electroluminescent display and displays video corresponding to content of an attraction. In accordance with an instruction from the control apparatus 500, the display 302 displays video that is synchronous with the operation of the attraction apparatus 200.

The gender input device 303 is a device for inputting the gender of a user. In the example illustrated in FIG. 5, the gender input device 303 has two buttons respectively representing male and female. The user or an attendant for the attraction can set the user's gender by pressing either of the buttons. The gender input device 303 is not limited to a button-type structure, as long as the user's gender can be input. The gender input device 303 may be provided in an apparatus other than the head-mounted display 300. For example, the attraction apparatus 200 or the control apparatus 500 may have an interface for inputting the gender.

Figure 6:
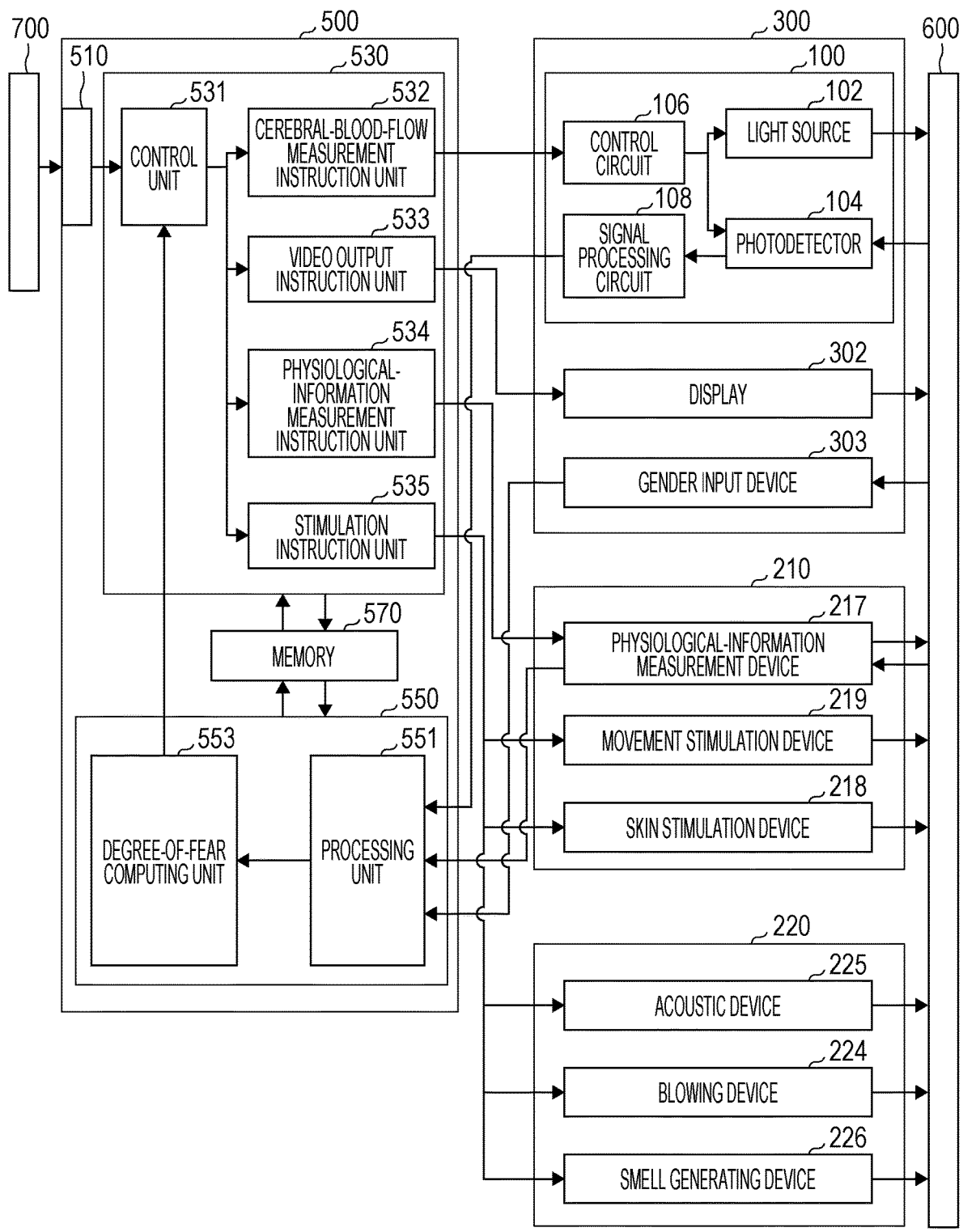
FIG. 6 is a diagram illustrating an example of a more detailed configuration of the attraction system.

FIG. 6 is a block diagram illustrating an example of a more detailed configuration of the control apparatus 500 and the head-mounted display 300 in the attraction system 10. The control apparatus 500 includes an input interface 510, a control circuit 530, a signal processing circuit 550, and a memory 570. The control circuit 530 includes a control unit 531, a cerebral-blood-flow measurement instruction unit 532, a video output instruction unit 533, a physiological-information measurement instruction unit 534, and a stimulation instruction unit 535. The signal processing circuit 550 includes a processing unit 551, a degree-of-fear computing unit 553. Each unit in the control circuit 530 and the signal processing circuit 550 does not have to be an independent circuit, and the control circuit 530 or the signal processing circuit 550 may be a function realized by executing a program stored in a recording medium, such as the memory 570.

In accordance with the program stored in the memory 570, the control circuit 530 controls the head-mounted display 300, the ride apparatus 210, and the stimulation unit 220. The signal processing circuit 550 calculates a degree of fear felt by the user 600, based on cerebral blood flow information, physiological information, and gender information obtained from the head-mounted display 300, and sends degree-of-fear information, which is information indicating the degree of fear felt by the user 600, to the control circuit 530. Based on the degree of fear felt by the user 600, the control circuit 530 transmits an instruction for adjusting stimuli to be given to the user 600 to the head-mounted display 300, the ride apparatus 210, and the stimulation unit 220.

Each of the control circuit 530 and the signal processing circuit 550 may be implemented by, for example, a circuit, such as a CPU, a graphical processing unit (GPU), or a digital signal processor (DSP). The control circuit 530 and the signal processing circuit 550 may be implemented by one integrated circuit. Processing in the control circuit 530 and the signal processing circuit 550 may be implemented by hardware, such as an application-specific integrated circuit (ASIC), instead of software.

The cerebral-blood-flow measurement instruction unit 532 transmits, to the control circuit 106 in the detecting apparatus 100 in the head-mounted display 300, a signal indicating that cerebral blood flow information of the user 600 is to be obtained. In response to the signal, the control circuit 106 in the detecting apparatus 100 causes the light source 102 to emit predetermined light.

The wavelength, the intensity, the illumination time, and the illumination pattern of the light emitted from the light source 102 are not particularly limiting. The wavelength of the light that is used may be a wavelength over which the cerebral blood flow information can be obtained. The light source 102 emits, for example, light having a wavelength that is larger than or equal to 650 nm and that is smaller than or equal to 950 nm. This wavelength range is included in the wavelength range of red to near-infrared light. This wavelength range is called the biological window and is known to have a low in-vivo absorption rate. Although the light source 102 in the present embodiment emits light in the above-described wavelength range, it may use light in another wavelength range. Terms for "light" are also used herein not only for visible light but also for infrared light.

The light source 102 may be, for example, a laser diode that repeatedly emits pulsed light or the like. When a laser light source is used as the light source 102, for example, a laser light source that satisfies class 1 of a laser safety standard formulated in each country is selected. When class 1 is satisfied, the light source 102 emits low-illuminance light with which the accessible emission level (AEL) falls below 1 mW. When the sensitivity of the photodetector 104 is insufficient due to the low-illuminance light, the light source 102 may repeatedly emit pulsed light, and the pulsed light may be repeatedly accumulated in the photodetector 104. The light source 102 is not limited to a laser light source and may be another type of light source, such as a light-emitting diode (LED). The light source 102 may be configured so as to emit steady light, not pulsed light.

The forehead portion of the user 600 is illuminated with the light from the light source 102. Part of the light propagates inside the forehead portion of the user 600 and is incident on the photodetector 104 as light including information of cerebral blood flow. The control circuit 106 controls the photodetector 104 in synchronization with the operation of the light source 102.

The photodetector 104 has, for example, a photodiode. In one example, the photodetector 104 may be an image sensor including a plurality of photodiodes arrayed two-dimensionally. Each photodiode outputs electrical signals corresponding to the amount of received light through photoelectric conversion. The photodetector 104 may include an amplifier for amplifying the electrical signals and an analog-to-digital converter for converting analog signals into digital signals. Signals output from the photodetector 104 are sent to the signal processing circuit 108.

The signal processing circuit 108 processes the signals output from the photodetector 104 and transmits the resulting signals to the control apparatus 500. There is a possibility that a signal outlier occurs owing to motion of the human body or the forehead portion of the user 600, or periodic noise that is thought to derive from a heart rate, pulse wave, or brain wave is introduced into a cerebral blood flow waveform. In such a case, accurate measurement of the cerebral blood flow is not realized. Accordingly, the signal processing circuit 108 generates data obtained by eliminating outliers or periodically varying components from the obtained signals and outputs the generated data.

The signal processing circuit 550 in the control apparatus 500 obtains the data from the signal processing circuit 108 in the detecting apparatus 100. The processing unit 551 in the signal processing circuit 550 calculates the concentration of oxygenated hemoglobin, based on the obtained data, and records the concentration to the memory 570 in association with the physiological information and the gender information of the user 600.

Video to be displayed on the display 302 of the head-mounted display 300 is output from the video output instruction unit 533 in the control apparatus 500. The control unit 531 controls the video output instruction unit 533. The control unit 531 selects appropriate video based on the information of the cerebral blood flow or the like of the user 600, the information being recorded in the memory 570, and issues an instruction for displaying the selected video on the display 302 via the video output instruction unit 533.

The gender input device 303 in the head-mounted display 300 is a device for obtaining the gender information of the user 600. For instance, in the example illustrated in FIG. 5, the gender input device 303 has a male button and a female button. When the attraction is started, the user 600 or an attendant 700 for the attraction apparatus 200 can set the gender of the user 600 by pressing either of the buttons. This gender information is transmitted to the signal processing circuit 550 in the control apparatus 500 and is stored in the memory 570.

Next, the configurations of the ride apparatus 210 and the stimulation unit 220 in the attraction apparatus 200 will be described in more detail.

The "ride apparatus" as used herein means a moving vehicle that a user can ride. The posture of the user 600 who has ridden the ride apparatus 210 may be either of a seated position and a standing position. Various types are available as the movement of the ride apparatus 210. Possible examples of the movement include (a) moving from a start point to a goal point, (b) moving from a start point and returning to the start point through a certain point, and (c) moving on the spot rather than moving from a start point. The movement of the ride apparatus 210 is not limited to any of these examples.

The physiological-information measurement device 217 in the ride apparatus 210 is arranged at a portion where the skin of the user 600 and the ride apparatus 210 contact each other. The physiological-information measurement device 217 obtains physiological information, such as a skin temperature, a skin electrical resistance, a heart rate, a pulse, and blood flow in subcutaneous blood vessels. The physiological-information measurement instruction unit 534 in the control apparatus 500 controls the physiological-information measurement device 217. The form of the physiological-information measurement device 217 differs depending on the type of physiological information that is measured. For measuring the skin temperature, the physiological-information measurement device 217 may include a thermographic device or a thermocouple. For measuring the skin electrical resistance, the physiological-information measurement device 217 may include two electrodes. For measuring the heart rate or pulse, the physiological-information measurement device 217 may include a three-axis motion sensor. For measuring the blood flow in subcutaneous blood vessels, the physiological-information measurement device 217 may include a near-infrared-light illumination device and a reflection-light detecting device. As described above, the physiological-information measurement device 217 may take various forms. The obtained physiological information is transmitted to the signal processing circuit 550 in the control apparatus 500 and is accumulated in the memory 570 for each user 600.

The skin stimulation device 218 is arranged at the position where the skin of the user 600 and the ride apparatus 210 contact each other. The skin stimulation device 218 includes electrically conductive material and gives an electrical stimulus to the user 600 at a particular timing. The stimulation instruction unit 535 in the control apparatus 500 controls the timing at which the stimulus is given and the intensity and the duration of the stimulus.

The movement stimulation device 219 is a device that gives a stimulus to the user 600 by using movement of the ride apparatus 210. Examples of the movement of the ride apparatus 210 for giving a stimulus to the user 600 include sudden acceleration, sudden deceleration, sudden stop, sudden turn, on-the-spot vibration, up-and-down movement, and rotational movement. The stimulation instruction unit 535 in the control apparatus 500 controls the types, intensities, timings, durations, and so on of those types of movement stimulus.

The blowing device 224 in the stimulation unit 220 is arranged in order to give a stimulus using wind, a heat stimulus using a warm wind, or a cold stimulus using a cold wind to the user 600. The stimulation instruction unit 535 in the control apparatus 500 controls the amount of the wind, the temperature of the wind, the timing of blowing the wind, and so on.

The acoustic device 225 mainly outputs audio data for video output onto the display 302 of the head-mounted display 300. The stimulation instruction unit 535 in the control apparatus 500 controls the audio volume of the audio data.

The smell generating device 226 has a plurality of types of low-molecular-compound solution that is a source of smell and has a blower for supplying volatile components thereof to the user 600. The smell generating device 226 mixes the individual volatile components that arise from the low-molecular-compound solutions in accordance with an intended smell and provides the smell to the user 600 over wind generated by the blower. The stimulation instruction unit 535 in the control apparatus 500 controls the timing at which the smell is provided to the user 600, the type of smell, and so.

(Operations)

Next, operations in the present embodiment will be described with reference to FIGS. 7 and 8.

Figure 7:
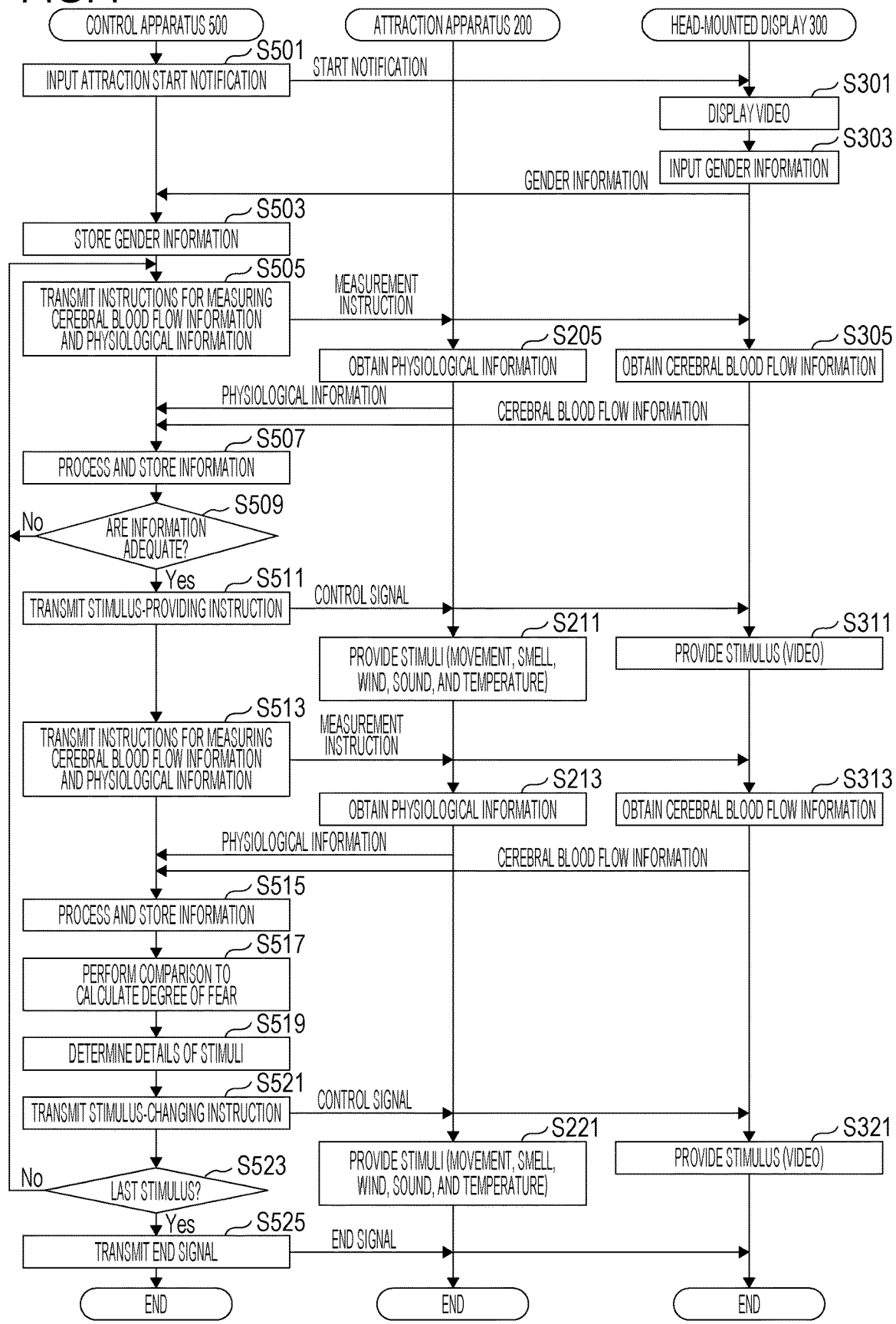
FIG. 7 is a flowchart illustrating a processing flow of the attraction system in the present embodiment.

FIG. 7 is a sequence diagram illustrating a processing flow of the attraction system in the present embodiment.

First, the attendant 700 for the attraction system inputs an attraction start notification via the input interface 510 in the control apparatus 500 (step S501). In response, a signal indicating the attraction start notification is transmitted from the control apparatus 500 to the display 302 of the head-mounted display 300. The display 302 displays video for notifying the user 600 that the attraction is to be started (step S301). This video includes an instruction for prompting the user 600 to input his or her gender. In accordance with the instruction, the user 600 operates the gender input device 303 to input the gender (step S303). Gender information indicating the gender is transmitted to the control apparatus 500 and is stored in the memory 570 (step S503).

Next, the cerebral-blood-flow measurement instruction unit 532 in the control apparatus 500 transmits an instruction indicating that cerebral blood flow information of the user 600 is to be measured to the head-mounted display 300, and the physiological-information measurement instruction unit 534 in the control apparatus 500 transmits an instruction indicating that physiological information of the user 600 is to be measured to the attraction apparatus 200 (step S505). This operation is performed in order to obtain the physiological information and the cerebral blood flow information of the user 600 in a normal state. In accordance with the instruction, the physiological-information measurement device 217 in the attraction apparatus 200 obtains the physiological information of the user 600 and transmits the physiological information to the control apparatus 500 (step S205). The detecting apparatus 100 in the head-mounted display 300 obtains the cerebral blood flow information of the user 600 in accordance with the instruction indicating that the cerebral blood flow information is to be measured and transmits the obtained cerebral blood flow information to the control apparatus 500 (step S305). This cerebral blood flow information is referred to as "first blood flow information". The processing unit 551 in the control apparatus 500 processes the obtained cerebral blood flow information and physiological information and stores the resulting cerebral blood flow information and physiological information in the memory 570 (step S507).

The processing unit 551 in the signal processing circuit 550 determines whether or not the cerebral blood flow information and the physiological information are adequate (step S509). When the cerebral blood flow information or the physiological information includes an anomalous value, the control apparatus 500 re-issues the instructions for measuring the cerebral blood flow information and the physiological information, the instruction issuance being performed in step S505. For instance, upon failing to properly obtain the cerebral blood flow information, the control apparatus 500 may cause the display 302 to display, for example, video for instructing the user to wear the head-mounted display 300 again. In this case, after the user 600 wears the head-mounted display 300 again, the head-mounted display 300 obtains the cerebral blood flow information again. When the obtained living-body information does not include an anomalous value, the process proceeds to step S511.

The control apparatus 500 transmits, to the attraction apparatus 200 and the head-mounted display 300 via the stimulation instruction unit 535 in the control circuit 530, a control signal for giving an instruction for providing stimuli (step S511). In accordance with the control signal, the head-mounted display 300 displays new video on the display 302 to provide a video stimulus to the user 600 (step S311). At the same time, in accordance with the control signal, the attraction apparatus 200 drives the ride apparatus 210 and the stimulation instruction unit 535 to give the user 600 stimuli, such as movement, smell, wind, sound, and temperature, for enhancing a sense of immersion into the video (step S211). These stimuli are collectively referred to as a "first stimulus".

Subsequently, in order to measure a degree of fear felt by the user 600 with respect to the new stimuli, the control apparatus 500 re-transmits the instructions for measuring the cerebral blood flow information and the physiological information to the head-mounted display 300 and the attraction apparatus 200 (step S513). The head-mounted display 300 and the attraction apparatus 200 respectively obtain the cerebral blood flow information and the physiological information of the user 600, based on the instructions, and respectively transmit the cerebral blood flow information and the physiological information to the control apparatus 500 (steps S313 and S213). The cerebral blood flow information obtained in S313 is referred to as "second blood flow information". The processing unit 551 in the control apparatus 500 processes the obtained cerebral blood flow information and physiological information. The processing unit 551 performs preprocessing, for example, removing periodic noise components, such as a heart rate or a brain wave, in the obtained cerebral blood flow information and removing outliers that occur due to violent body movement. The processed information is stored in the memory 570 (step S515).

Next, the signal processing circuit 550 in the control apparatus 500 compares the information stored in step S507 with the information stored in S515 to calculate a degree of fear felt by the user 600 (step S517). For example, the signal processing circuit 550 calculates an amount of change between the first blood flow information stored in step S507 and the second blood flow information stored in step S515. The process in S517 is performed by the degree-of-fear computing unit 553. This amount of change reflects the degree of fear felt by the user 600. The control circuit 530 in the control apparatus 500 determines details of stimuli according to the calculated degree of fear felt by the user 600 (step S519). For example, the control circuit 530 compares the above-described amount of change with a threshold pre-set for each gender and determines details of the stimuli to be provided to the user based on the result of the comparison. The control apparatus 500 transmits, to the attraction apparatus 200 and the head-mounted display 300 via the stimulation instruction unit 535 in the control circuit 530, a control signal for giving an instruction for making changes to the stimuli (step S521).

FIG. 8 is a flowchart specifically illustrating examples of the processes in steps S517 and S519. In the present embodiment, the concentrations of oxygenated hemoglobin in the prefrontal area, particularly, in the left and right ventrolateral prefrontal cortices, are used in order to determine the degree of fear. The signal processing circuit 550 in the control apparatus 500 calculates the concentrations of oxygenated hemoglobin in the prefrontal area before and after the stimuli are provided and calculates an amount of change ΔOxy therebetween (step S801). The "amount of change" as used in this case means a difference or a rate of change. Subsequently, the degree-of-fear computing unit 553 in the signal processing circuit 550 refers to the gender information, recorded in the memory 570, to determine whether the user 600 is male or female (step S802). If the user 600 is male, the degree-of-fear computing unit 553 refers to a threshold S1 for the amount of change in the oxygenated hemoglobin to compare ΔOxy with the threshold S1 (step S803). If ΔOxy is larger than S1, it is determined that the degree of fear felt by the user 600 is high (step S805). Conversely, if ΔOxy is smaller than or equal to S1, it is determined that the degree of fear felt by the user 600 is low (step S806). On the other hand, if the gender of the user 600 is female, the degree-of-fear computing unit 553 uses S2, which is larger than S1, as a threshold for the determination to compare ΔOxy with S2 (step S804). If ΔOxy is larger than S2, it is determined that the degree of fear felt by the user 600 is high (step S805). Conversely, if ΔOxy is smaller than or equal to S2, it is determined that the degree of fear felt by the user 600 is low (step S807). By referring to prepared stimulus determination criteria, the control unit 531 in the control apparatus 500 determines details of next stimuli to be provided to the user 600, in accordance with whether the degree of fear felt by the user 600 is high or low (step S809).

The stimulus determination criteria may be, for example, data that specifies operations as in Table 2 below.

TABLE 2

| | | Magnitude of Degree of Fear | |
| --- | --- | --- | --- |
| | | Degree of Fear: High | Degree of Fear: Low |
| Head-Mounted Display | Video | Provide video with approximately the same stimulus intensity as the previous video | Provide video in which the degree of fear is increased relative to the previous stimulus |
| Stimulation Unit | Sound | Provide sound stimulus that is approximately the same as the previous stimulus | Increase audio volume or provide music that inspires fear |
| | Movement | Provide movement stimulus that is approximately the same as the previous stimulus | Accelerate or decelerate more suddenly or provide movement with larger range of swing than the previous stimulus |
| | Smell | N/A | Provide smell that suits the video |
| | Wind | N/A | Provide wind at timing that suits the video |
| | Temperature | N/A | Provide warm wind or cold wind that suits the video |
| | Electricity | N/A | Provide electrical stimulus at timing that suits the video |

If it is determined that the degree of fear is high, the intensities of the stimuli after the determination are maintained to be approximately the same as the intensities of the stimuli before the determination. On the other hand, if it is determined that the degree of fear is low, the sense of satisfaction of the user 600 about the attraction apparatus is estimated to be insufficient. Thus, for example, stimuli for enhancing the degree of fear about the video or the sense of immersion into the video, relative to the stimuli before the determination, are added (steps S221 and S321). As described above, the intensity or the type of each stimulus to be provided from the attraction apparatus to the user is appropriately changed based on a result of the comparison of the first amount of change with the threshold.

Although an operation for making changes to the stimuli based only on a change between the pieces of blood flow information has been described above by way of example, the pieces of physiological information respectively obtained in steps S205 and S213 may also be considered. For example, the amount of change between the pieces of physiological information respectively obtained in steps S205 and S213, in addition to the determinations in steps S803 and S804 in FIG. 8, may also be considered in combination to determine the psychological state of the user. In this case, details of changes in the stimuli to be given to the user are determined based on both the amount of change between the pieces of blood flow information and the amount of change between the pieces of physiological information.

After the stimuli are provided, the control unit 531 determines the progress of the attraction and determines whether or not the provision of a last stimulus is completed (step S523). If the provision of the last stimulus is not completed, the process returns to step S503, and the same operation is executed with respect to next stimuli. When the provision of the last stimulus is completed, the control apparatus 500 transmits a signal indicating the end of the attraction to the attraction apparatus 200 and the head-mounted display 300 (step S525). In response to the signal, the head-mounted display 300 displays video indicating the end of the attraction to notify the user 600 that the attraction is ended.

(Advantages and Modifications)

As described above, the control apparatus 500 in the present embodiment obtains the cerebral blood flow information from the detecting apparatus 100 and controls the operation of the attraction apparatus 200 based on the cerebral blood flow information. The cerebral blood flow information includes information indicating the concentration of oxygenated hemoglobin in blood in the user's brain. In accordance with a change in the cerebral blood flow information, the control apparatus 500 changes the intensity or the type of at least one stimulus to be provided to the user. More specifically, the control apparatus 500 detects a change between the pieces of cerebral blood flow information before and after the attraction apparatus 200 provides one stimulus to the user, and when the magnitude of the change is smaller than or equal to a threshold, the control apparatus 500 increases the intensity of the stimulus to be provided to the user. The threshold is set to a value that differs depending on the user's input gender.

With such a configuration, details of the stimuli to be provided to each user are appropriately adjusted according to the degree of fear felt by the user, thus making it possible to enhance the individual's sense of satisfaction. For example, it is possible to enhance the emotion of wanting to share the same attraction with a family or a partner. Also, one attraction can provide a user with a sense of satisfaction corresponding to the individual's preference.

The embodiment described above is merely an example, and various modifications may be made to the above-described embodiment. For example, the attraction apparatus 200 does not necessarily have to be divided into the ride apparatus 210 and the stimulation unit 220. Using the head-mounted display 300 is not an essential requirement, either. The detecting apparatus 100 and the display 302 may also be included in the attraction apparatus 200. Using the gender input device 303 and the physiological-information measurement device 217 is not an essential requirement, either. The stimuli given to the user are not limited to the above-described examples and may be any forms as long as they stimulate at least one of the user's five senses, such as the visual sense, auditory sense, tactile sense, and olfactory sense. Some of the display 302, the movement stimulation device 219, the skin stimulation device 218, the acoustic device 225, the blowing device 224, and the smell generating device 226 in the above-described embodiment may be omitted, and a device that provides a stimulus that differs from those described above may also be used.

Second Embodiment

Next, an example of an attraction system that performs control that differs depending on the age group of a user.

In a second embodiment, information of the age group, in addition to the gender, is used as attribute information. The control circuit 530 obtains attribute information indicating the gender and the age group of a user and determines a threshold for the amount of change in the blood flow information of the user based on the obtained attribute information. In accordance with the age group of the user, the control circuit 530 determines the size of an area in the frontal region from which the blood flow information is obtained.

The divisions of the age groups are age group 1 (aged about 6 years or younger), age group 2 (ages of elementary school students or older, and ages younger than 65 years), and age group 3 (aged 65 years or older). The age group of each user is input via the input interface 510 in the attraction system. The user or a third party, such as an attendant, may perform the input. The age group may also be determined through image processing, based on an image acquired by a camera included in the attraction system. Similarly, the gender may be determined based on an image acquired by the camera. The photodetector 104 in the detecting apparatus 100 may have the functions of the camera.

In the case of age group 3, the amount of change in the cerebral blood flow during task execution tends to decrease. Also, since the brain function localization becomes fuzzy, the cerebral blood flow information in the brain area in the entire forehead area is used. That is, the amount of change is calculated based on a detection result of the entire forehead area. For example, an average value of the amounts of change in the cerebral blood flow information in the entire area of the forehead may be used. The threshold for the amount of change is set low, compared with a threshold for age group 2.

In the case of age group 1, since the brain function localization is still fuzzy, data of the amounts of change in the cerebral blood flow obtained from the entire forehead area is used in order to calculate a representative value. For example, an average value may be used. Although age group 1 is sensitive to stimuli, compared with age group 2, the amount of change in the cerebral blood flow is almost the same as that in the case of age group 2. Accordingly, for age group 1, the threshold for the amount of change in the cerebral blood flow information is set to a value that is substantially the same as the threshold for age group 2.

In the present embodiment, before the operation of the attraction or at an initial stage of the operation of the attraction, a preliminary stimulus is given to the user. Examples of the preliminary stimulus include an image, sound, smell, and vibration, which are known to evoke emotion that is equivalent to emotion to be detected during the attraction. The preliminary stimulus is given to, for example, only age group 2. The amount of change in the cerebral blood flow when the preliminary stimulus is given is measured. An area in which the cerebral blood flow is measured during operation of the attraction is determined based on a result of the measurement.

FIG. 9 is a flowchart illustrating some of operations in the present embodiment. In the present embodiment, the operations in FIG. 9 are executed before the attraction is started, after the attraction is started, or before step S505 in FIG. 7 is executed. Other operations are analogous to the operations illustrated in FIG. 7.

In step S901, the age group of a user is determined. If it is determined that the age group of the user is age group 1 or 3, the process proceeds to step S902.

In step S902, the measurement area of the user is set to the entire area of the forehead portion. Next, in step S903, the age group of the user is determined. If the age group of the user is age group 1, the process proceeds to step S906, and if the age group of the user is age group 3, the process proceeds to step S904. In step S904, a set of thresholds S1 and S2 for age group 3 is set. S1 is a threshold for females, and S2 is a threshold for males.

If it is determined in step S901 that the age group of the user is age group 2, the process proceeds to step S905. In step S905, a preliminary stimulus is provided, and based on a result of measurement of cerebral blood flow at this point in time, the measurement area is determined. The preliminary stimulus may be, for example, the same type of stimulus as a stimulus that the attraction gives to the user. The preliminary stimulus may herein be referred to as a "second stimulus". The measurement area that is determined is, for example, an area in which the amount of change in the oxygenated hemoglobin concentration with respect to the preliminary stimulus is the largest. Next, in step S906, a set of thresholds S1 and S2 is set. The set of thresholds S1 and S2 is set to different values depending on whether the age group of the user is age group 1 or 2.

The set of thresholds S1 and S2 determined for each user, as described above, is used in step S517 in FIG. 7. In the present embodiment, since the thresholds S1 and S2 are set considering not only the user's gender but also the age group, it is possible to more appropriately determine the psychological state of the user.

Also, when the age group of the user is age group 1 or 3, the entire area of the forehead portion is set for the measurement area, and when the age group of the user is age group 2, a part of the forehead portion is set for the measurement area. When the age group of the user is age group 2, obtaining the first blood flow information in step S305 is preceded by operations below:
(1) obtaining third blood flow information of the user by using the detecting apparatus;
(2) providing a second stimulus, which is a preliminary stimulus, to the user by using the attraction apparatus;
(3) obtaining fourth blood flow information of the user by using the detecting apparatus, after the second stimulus is provided;
(4) obtaining a second amount of change indicating a difference between the third blood flow information and the fourth blood flow information; and
(5) determining at least one area in the frontal region which is to be illuminated with light during obtaining of the first blood flow information in step S305 and during obtaining of the second blood flow information in step S313, based on the second amount of change.

With such operations, a portion in which a change in the blood flow of the user is large can be measured in steps S305 and S313. Thus, it is possible to estimate the psychological state of the user with higher accuracy.

With the above-described operations, the attraction apparatus can be more appropriately controlled according to the age group of each user.

Although attribute information of both the gender and the age group is used in the second embodiment, only the information of the age group may be used to perform similar operations. In this case, the thresholds S1 and S2 described above may be set to the same value.

The above description has been given of attraction apparatuses that are mainly installed at amusement facilities. The technology disclosed herein, however, can be applied to apparatuses for entertainment purposes which are installed at places other than amusement facilities. For example, the technology disclosed herein may also be applied to controlling apparatuses, such as home video game consoles or virtual reality appliances, that have a function of providing at least one of stimuli, such as the visual sense, tactile sense, auditory sense, and olfactory sense, to users.

What is claimed is:
1. A control method for a blood-flow-information detection system including:
a stimulation device that provides a stimulus to a user;
a light source that emits light to an illuminated region of the user; and
a photodetector that detects reflection light that returns from a measurement region of the user
the control method comprising:
causing the light source to emit the light to a first illuminated area in a frontal region of a head of the user;
causing the stimulation device to provide the stimulus to the user;
detecting first blood flow information indicating a state of blood flow of the user based on first reflection light that returns from a first measurement area in the frontal region, when the stimulus is provided and/or after the stimulus is provided;
changing the measurement region from the first measurement area to a second measurement area in the frontal region, based on the first blood flow information; and
detecting second blood flow information after detecting the first blood flow information based on second reflection light that returns from the second measurement area.

2. The control method according to claim 1, further comprising:
changing the illuminated region from the first illuminated area to a second illuminated area in the frontal region, based on the first blood flow information.

3. The control method according to claim 1, further comprising:
detecting third blood flow information of the user, before the stimulation device is caused to provide the stimulus to the user,
wherein the changing of the measurement region is performed based on a result of comparison between the first blood flow information and the third blood flow information.

4. The control method according to claim 1, wherein the blood-flow information detection system comprises an attraction system.

5. A non-transitory computer-readable recording medium storing therein a program for controlling a blood-flow-information detection system including:
a stimulation device that provides a stimulus to a user;
a light source that emits light to an illuminated region of the user; and
a photodetector that detects reflection light that returns from a measurement region of the user,
wherein the program, when executed by a computer, causes the computer to execute:
causing the light source to emit the light to a first illuminated area in a frontal region of a head of the user;
causing the stimulation device to provide the stimulus to the user;
detecting first blood flow information indicating a state of blood flow of the user based on first reflection light that returns from a first measurement area in the frontal region, when the stimulus is provided and/or after the stimulus is provided;
changing the measurement region from the first measurement area to a second measurement area in the frontal region, based on the first blood flow information; and
detecting second blood flow information after detecting the first blood flow information, based on second reflection light that returns from the second measurement area.

6. A blood-flow-information detection system comprising:
a stimulation device that provides a stimulus to a user;
a light source that emits light to an illuminated region of the user;
a photodetector that detects reflection light that returns from a measurement region of the user; and
a processing circuit,
wherein
the processing circuit
causes the light source to emit the light to a first illuminated area in a frontal region of a head of the user;
causes the stimulation device to provide the stimulus to the user;
detects first blood flow information indicating a state of blood flow of the user based on first reflection light that returns from a first measurement area in the frontal region, when the stimulus is provided and/or after the stimulus is provided;
changes the measurement region from the first measurement area to a second measurement area in the frontal region, based on the first blood flow information; and detects second blood flow information after detecting the first blood flow information, based on second reflection light that returns from the second measurement area.

7. The control method according to claim 1, further comprising:

controlling the amount of stimulus provided to the user based on the first blood flow information.

8. The control method according to claim 1, wherein the first blood flow information indicates hemoglobin concentration, and the changing of the measurement region is performed based on a change of the hemoglobin concentration with respect to the stimulus.

9. The control method according to claim 1, wherein the stimulus includes at least one selected from the group consisting of video, sound, movement, tactile sensation, and smell.

\* \* \* \* \*